United States Patent
Haderlein et al.

(10) Patent No.: US 8,058,466 B2
(45) Date of Patent: Nov. 15, 2011

(54) METHOD FOR PRODUCING 3-PENTENENITRILE BY MEANS OF THE HYDROCYANATION OF 1,3-BUTADIENE

(75) Inventors: Gerd Haderlein, Grünstadt (DE); Tobias Aechtner, Mannheim (DE); Andreas Leitner, Ludwigshafen (DE); Hermann Luyken, Ludwigshafen (DE); Peter Pfab, Neustadt (DE); Jens Scheidel, Hirschberg (DE); Andrea Haunert, Mannheim (DE); Thomas Genger, Lambsheim (DE)

(73) Assignee: BASF SE, Ludwigshafen (DE)

( * ) Notice: Subject to any disclaimer, the term of this patent is extended or adjusted under 35 U.S.C. 154(b) by 439 days.

(21) Appl. No.: 12/376,731

(22) PCT Filed: Aug. 1, 2007

(86) PCT No.: PCT/EP2007/057926
§ 371 (c)(1),
(2), (4) Date: Feb. 6, 2009

(87) PCT Pub. No.: WO2008/017626
PCT Pub. Date: Feb. 14, 2008

(65) Prior Publication Data
US 2009/0247779 A1    Oct. 1, 2009

(30) Foreign Application Priority Data

Aug. 8, 2006 (EP) .................................... 06118612

(51) Int. Cl.
*C07C 253/10* (2006.01)
(52) U.S. Cl. ........................................................ 558/335
(58) Field of Classification Search ........................ None
See application file for complete search history.

(56) References Cited

U.S. PATENT DOCUMENTS

| | | |
|---|---|---|
| 3,496,215 A | 2/1970 | Drinkard et al. |
| 4,810,815 A | 3/1989 | Bryndza |
| 7,781,608 B2 * | 8/2010 | Scheidel et al. ............... 558/335 |
| 2007/0155977 A1 | 7/2007 | Jungkamp et al. |

FOREIGN PATENT DOCUMENTS

| | | |
|---|---|---|
| CA | 2552862 | 8/2005 |
| DE | 102004004671 | 8/2005 |
| DE | 102004004684 | 8/2005 |
| DE | 102004004724 | 8/2005 |
| WO | WO-2005073175 | 8/2005 |

OTHER PUBLICATIONS

Tolman et al., "Advances in Catalysis", vol. 33, pp. 1-46, 1985.

* cited by examiner

*Primary Examiner* — Kamal Saeed
(74) *Attorney, Agent, or Firm* — Connolly Bove Lodge & Hutz LLP

(57) ABSTRACT

An process for preparing 3-pentenenitrile by hydrocyanating 1,3-butadiene, in which the process yield with regard to recycled 1,3-butadiene is maximized.

9 Claims, 2 Drawing Sheets

US 8,058,466 B2

METHOD FOR PRODUCING 3-PENTENENITRILE BY MEANS OF THE HYDROCYANATION OF 1,3-BUTADIENE

CROSS REFERENCE TO RELATED APPLICATIONS

This application is a National Stage of PCT/EP2007/057926 filed Aug. 1, 2007 which in turn claims priority from European Application 06118612.8 filed Aug. 8, 2006, the entire contents of which are incorporated herein by reference.

FIELD OF THE INVENTION

The present invention relates to an improved process for preparing 3-pentenenitrile by hydrocyanating 1,3-butadiene with hydrogen cyanide in the presence of nickel(0) complexes having phosphorus ligands. In this process, 1,3-butadiene which comprises a stabilizer and is dried by azeotropic distillation is used.

BACKGROUND

Adiponitrile is an important starting material in nylon production, which is obtained by double hydrocyanation of 1,3-butadiene. In a first hydrocyanation, 1,3-butadiene is hydrocyanated to 3-pentenenitrile, while the by-products obtained are mainly 2-methyl-3-butenenitrile, 4-pentenenitrile, 2-pentenenitriles, 2-methyl-2-butenenitriles, $C_9$ nitriles and methylglutaronitrile. In a second, subsequent hydrocyanation, 3-pentenenitrile is reacted with hydrogen cyanide to give adiponitrile. Both hydrocyanations are catalyzed by nickel(0)-phosphorus complexes.

A general review of nickel-catalyzed olefin hydrocyanation is described in Tolman et al., Adv. Cat. 33, 1-46 (1985).

The hydrocyanation of 1,3-butadiene using a nickel catalyst of the formula $Ni[P(OR)_3]_4$ is described in U.S. Pat. No. 3,496,215. A disadvantage of this process is that no suitable technique is specified for the complete recovery of the 1,3-butadiene or of the catalyst.

The performance of the hydrocyanation in one or more reactors and their connection is described in U.S. Pat. No. 4,810,815, and mention is made of the possibility of continuous operation of stirred tanks or batteries of stirred tanks, but only a semibatchwise mode is described in detail in examples, from which the person skilled in the art cannot discern directly the conditions under which the method should proceed in continuous stirred tanks.

A process for removing organic phosphorus compounds and their metal complexes from organic nitriles in the hydrocyanation of olefins is described in DE 10 2004 004671. The removal is effected by contacting the product with a cycloparaffin or paraffinic hydrocarbon. This forms a liquid multiphase system.

1,3-Butadiene can polymerize. Therefore, stabilizers, for example tert-butylpyrocatechol (TBC), are added to the 1,3-butadiene.

The nickel(0) complexes used for the hydrocyanation of 1,3-butadiene are water-sensitive. Water-comprising 1,3-butadiene therefore has to be dried before the hydrocyanation.

DE-A-10 2004 04684 discloses the drying of 1,3-butadiene comprising water and a stabilizer with the aid of microporous solids. This adsorbs not only the water, but also the stabilizer, at least partly from the solids. Suitable microporous solids are aluminum oxide and molecular sieves.

Heterogeneous dessicants, as a result of the adsorption of stabilizers, have the disadvantage that, at least temporarily, 1,3-butadiene which is insufficiently stabilized, if at all, forms, and is subject to safety restrictions. For instance, unstabilized 1,3-butadiene can be used only at temperatures below 15° C. In addition, a further disadvantage is that the microporous adsorbents have to be regenerated regularly.

In addition, it is crucial for an integrated process for preparing 3-pentenenitrile, in which both 1,3-butadiene and the hydrocyanation catalyst stream are recycled, that the 1,3-butadiene used in a molar excess relative to hydrogen cyanide is recycled efficiently.

DE-A-10 2004 04724 discloses the reaction of stabilized 1,3-butadiene, which has been dried with the aid of microporous solids, with hydrocyanic acid in the presence of nickel(0) catalysts to give 3-pentenenitrile. Three distillation columns serve for the removal and recycling of unconverted 1,3-butadiene and of nickel(0) catalyst.

BRIEF SUMMARY

It is therefore an object of the present invention to remedy the aforementioned disadvantages and to provide an integrated process for preparing 3-pentenenitrile by hydrocyanating 1,3-butadiene, in which the process yield with regard to recycled 1,3-butadiene is at a maximum.

This object is achieved by a process for preparing 3-pentenenitrile by hydrocyanating 1,3-butadiene, which comprises the following process steps (FIG. 1):

(b') distillation of 1,3-butadiene comprising water, 1- and 2-butenes and a stabilizer in a distillation apparatus K4 to obtain a stream 15 as the bottom product, which comprises dried 1,3-butadiene, 1- and 2-butenes and the stabilizer, and a stream 16 as the top product, which comprises an azeotropic 1,3-butadiene/water mixture, condensation of the stream 16 in a condenser W, transfer of the resulting condensate (stream 17) into a phase separation apparatus, recycling of the upper liquid phase (stream 18) consisting of 1,3-butadiene as reflux to the column K4, and discharge of the lower liquid aqueous phase (stream 19), (a) reaction of stream 15 in a reactor R1 with hydrogen cyanide over at least one catalyst (stream 6d) to obtain a stream 1 which comprises 3-pentenenitrile, 2-methyl-3-butenenitrile, the at least one catalyst, unconverted 1,3-butadiene, and 1- and 2-butenes, with or without residues of unconverted hydrogen cyanide, (b) distillation of stream 1 in a distillation apparatus K1 to obtain a stream 2 as the top product, which comprises the predominant portion of the 1,3-butadiene from stream 1, and to obtain a stream 3 as the bottom product, which comprises 3-pentenenitrile, the at least one catalyst, 2-methyl-3-butenenitrile, 1- and 2-butenes and the remaining proportion of the 1,3-butadiene from stream 1 which has not been removed in stream 2;

(c) distillation of stream 3 in a distillation apparatus K2 to obtain a stream 5 at a side draw of the column, which 3-pentenenitrile and 2-methyl-3-butenenitrile, a stream 6 as the bottom product, which comprises the at least one catalyst, and a stream 4 as the top product, (d) compression of stream 4 in the compressor V1, discharge of a gaseous substream 4b which comprises 1- and 2-butenes, transfer of the compressed stream 4a into the condenser W1, combined condensation of this stream with stream 2 from b) and transfer of the condensate as stream 9, partly as reflux to the column K1 (stream 9b), partly as return stream into the reactor R1 (stream 9a), and (e) distillative separation of stream 5 to obtain 3-pentenenitrile and 2-methyl-3-butenenitrile.

DETAILED DESCRIPTION OF THE PREFERRED EMBODIMENTS

Figure 1:
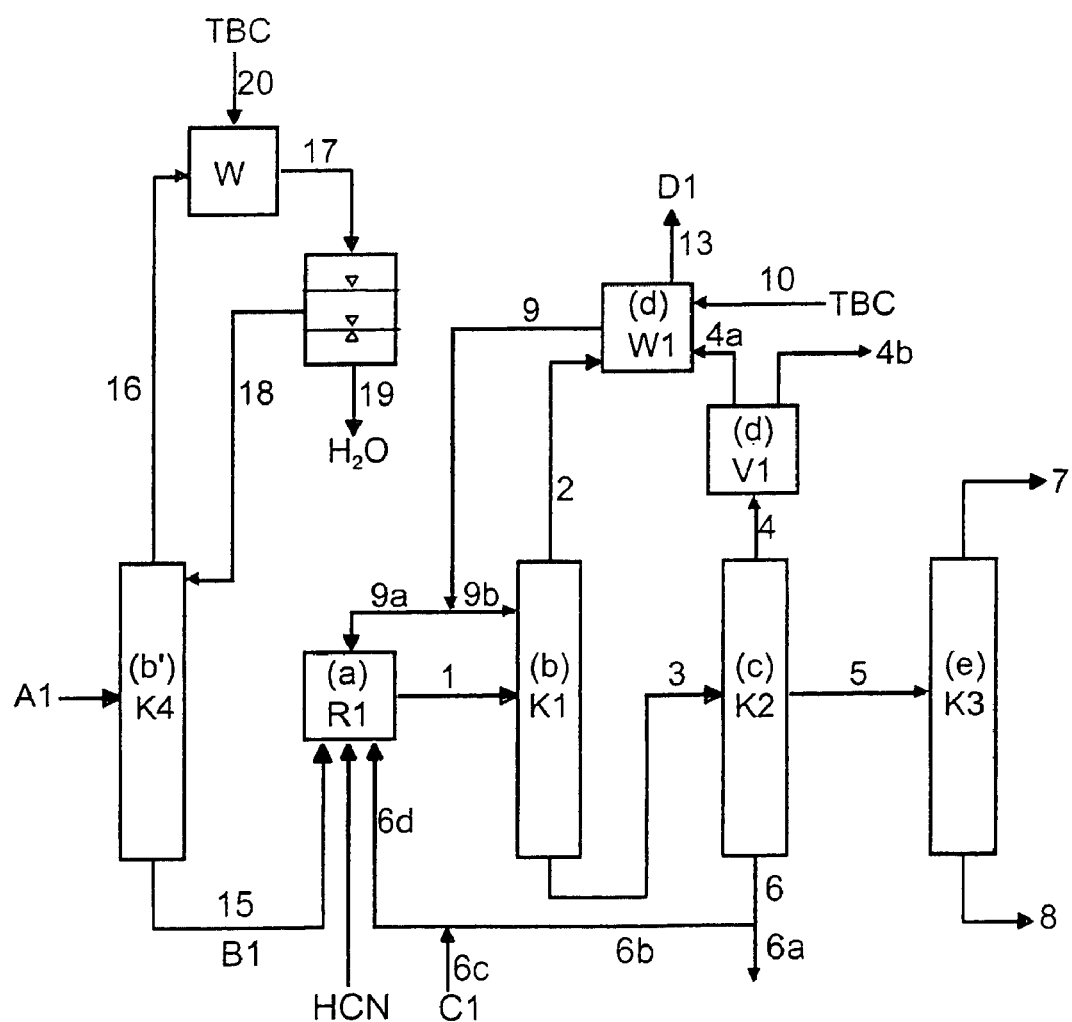
FIG. 1 is a schematic diagram depicting an embodiment of a process for preparing 3-pentenenitrile by hydrocyanating 1,3-butadiene.

In a preferred embodiment, the stream 6 obtained in step c) is divided into a recycle stream 6b and a discharge stream 6a. In a particularly preferred embodiment, a stream 6c which comprises fresh catalyst and, if appropriate, regenerated catalyst from stream 6a is added to stream 6b. The stream 6d thus obtained is used as the catalyst feed in process stage a).

The fraction which has been referred to above as the predominant portion of the 1,3-butadiene from stream 1 and is removed with stream 2 relates to a proportion of preferably more than 50%, more preferably more than 60%, in particular more than 70%, of the 1,3-butadiene which is present in stream 1. The 1,3-butadiene from stream 1 which correspondingly remains is transferred via stream 3 into process step (c).

Process step (b') serves for the dewatering of the 1,3-butadiene which also comprises 1- and 2-butenes and a stabilizer. This dewatering is based on the fact that butadiene and water form a heteroazeotrope which, on condensation, divides into a butadiene-rich phase and a water-rich phase. The two phases comprise in each case only small residual amounts of the other component.

The stabilizer used may be, for example, tert-butylpyrocatechol (TBC) or 2,6-di-tert-butyl-para-cresol (Ullmann's Encyclopedia of Industrial Chemistry, 6th Edition, 2000 Electronic Release, Chapter "Butadiene Stabilization, Storage and Transportation"). In the present document, the stabilizer is in each case referred to as TBC or stabilizer for short.

For the dewatering, the 1,3-butadiene is transferred into a distillation apparatus K4. In this distillation apparatus, a distillation is effected to obtain a stream 16 as the top product, which comprises the butadiene/water azeotrope, and a stream 15 as the bottom product, which comprises dewatered 1,3-butadiene, 1- and 2-butenes and the stabilizer.

Process step (b') of the process according to the invention can be performed in any suitable apparatus known to those skilled in the art. Suitable apparatus for the distillation is that as described, for example, in: Kirk-Othmer, Encyclopedia of Chemical Technology, 4th Ed., Vol. 8, John Wiley & Sons, New York, 1996, pages 334-348, such as sieve tray columns, bubble-cap tray columns, columns with structured packings, columns with random packings, or single-stage evaporators such as falling-film evaporators, thin-film evaporators, flash evaporators, multiphase helical tube evaporators, natural circulation evaporators or forced circulation flash evaporators. The distillation can be performed in a plurality of, such as two or three, apparatuses, preferably in a single apparatus.

In a preferred embodiment of the process according to the invention, column internals with structured packings are present in the distillation apparatus, which preferably generate between 2 and 60, more preferably between 3 and 40, in particular between 4 and 20 theoretical plates.

In a further preferred embodiment of the process according to the invention, the condensation at the top of the distillation apparatus is performed in such a way that a substream from the top effluent is flushed back into the condenser.

In a further preferred embodiment of the process according to the invention, the distillation can be performed with a direct condenser, so that the condensation is performed in a column section which is preferably equipped with a structured column packing, a collecting cup below this packing, a liquid draw from the collecting cup, a pumped circulation system with pump and heat exchanger connected to the liquid draw, and at least one device for introducing the liquid pumped in circulation to the packing above the collecting cup.

The distillation is performed at pressures of from 0.001 to 100 bar, preferably from 0.01 to 10 bar, in particular from 0.5 to 5 bar.

In process step (b'), the top product obtained from column K4 is a stream 16 which comprises butadiene and water. This stream 16 has the equilibrium composition of 1,3-butadiene and water at the particular distillation pressure.

Stream 16 is condensed into a condenser W. In order to stabilize the 1,3-butadiene present in the condensate (stream 17), stabilizer can be fed to the condenser (stream 20). In order to keep the amounts of stabilizer low, preference is given to condensing at temperatures below 15° C.

The condensate from condenser W is passed into a phase separation apparatus. There, the liquid organic phase is separated from the liquid aqueous phase. The organic phase (stream 18) is conducted as reflux at the top of column K4. The aqueous phase (stream 19) is discharged from the process. Small amounts of 1,3-butadiene still present in the aqueous phase may be driven out, for example by stripping or heating, and recycled into the condenser.

The bottom product obtained from column K4 is a stream 15 which comprises dried 1,3-butadiene, 1- and 2-butenes and stabilizer. This stream preferably has a residual content of water of <1000 ppm by weight, preferably <100 ppm by weight, more preferably <50% by weight ppm, based on the overall stream.

Process step (a) comprises the reaction of 1,3-butadiene dried by azeotropic distillation (stream 15) with anhydrous hydrogen cyanide over at least one catalyst (stream 6d) in the presence of at least one stabilizer. The catalyst used comprises homogeneously dissolved nickel complexes. The term "catalyst" should be understood to mean a mixture of nickel (0) complex and phosphorus ligand.

The Ni(0) complexes which comprise phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

$$P(X^1R^1)(X^2R^2)(X^3R^3) \tag{I}$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1R^2R^3)$ with the definitions of $R^1$, $R^2$ and $R^3$ specified in this description.

If two of the $X^1$, $X^2$ and $X^3$ groups are single bonds and one is oxygen, compound I is a phosphinite of the formula $P(OR^1)$ $(R^2)(R^3)$ or $P(R^1)(OR^2)(R^3)$ or $P(R^1)(R^2)(OR^3)$ with the definitions of $R^1$, $R^2$ and $R^3$ specified below.

If one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia

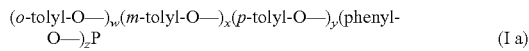

$(o\text{-tolyl-O}—)_w(m\text{-tolyl-O}—)_x(p\text{-tolyl-O}—)_y(\text{phenyl-O}—)_zP$ (I a)

where w, x, y and z are each a natural number where $w+x+y+z=3$ and $w, z \leq 2$.

Such compounds I a are, for example, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained by reacting a mixture comprising m-cresol and p-cresol, in particular in a molar ratio of 2:1, as obtained in the distillative workup of crude oil, with a phosphorus trihalide, such as phosphorus tri-chloride.

In another, likewise preferred embodiment, the phosphorus ligands are the phosphites, described in detail in DE-A 199 53 058, of the formula I b:

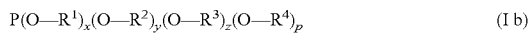

$P(O—R^1)_x(O—R^2)_y(O—R^3)_z(O—R^4)_p$ (I b)

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that $x+y+z+p=3$.

Preferred phosphites of the formula I b can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The $R^4$ radical is preferably phenyl. p is preferably zero. For the indices x, y and z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by
a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1H$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1H$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

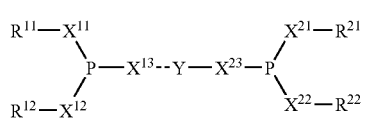

where
$X^{11}, X^{12}, X^{13} X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$: may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in German patent application DE 103 50 999, which has an earlier priority date but had not been published at the priority date of the present application.

The compounds I, I a, I b and II described and their preparation are known per se. The phosphorus ligands used may also be mixtures comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

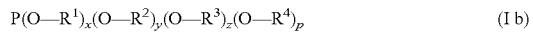

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that x+y+z+p=3; and mixtures thereof.

Process step (a) of the process according to the invention can be performed in any suitable apparatus known to those skilled in the art. Useful apparatus for the reaction is thus customary apparatus, as described, for example, in: Kirk-Othmer, Encyclopedia of Chemical Technology, 4th Ed., Vol. 20, John Wiley & Sons, New York, 1996, pages 1040 to 1055, such as stirred tank reactors, loop reactors, gas circulation reactors, bubble column reactors or tubular reactors, in each case, if appropriate, with devices for removing heat of reaction. The reaction can be performed in a plurality of, such as 2 or 3, apparatuses.

In a preferred embodiment of the process according to the invention, reactors having backmixing characteristics or batteries of reactors having backmixing characteristics have been found to be useful. Particularly advantageous reactors have been found to be loop reactors (see DE 10 2004 004673).

The hydrocyanation can be performed in the presence or in the absence of a solvent. When a solvent is used, the solvent should be liquid at the given reaction temperature and the given reaction pressure and be inert toward the unsaturated compounds and the at least one catalyst. In general, the solvents used are hydrocarbons, for example benzene or xylene, or nitriles, for example acetonitrile, benzonitrile, or pentenenitriles such as 2-, 3- and 4-pentenenitriles.

The reaction can be performed in batchwise mode, continuously or in semibatchwise mode.

Preference is given to performing the hydrocyanation continuously in one or more stirred process steps. When a multitude of process steps is used, it is preferred that the process steps are connected in series. In this case, the product is transferred from one process step directly into the next process step. The hydrogen cyanide can be fed directly into the first process step or between the individual process steps of the hydrocyanation reaction (a).

The reaction is performed preferably at absolute pressures of from 0.1 to 100 MPa, more preferably from 0.5 to 50 MPa, in particular from 1 to 5 MPa. The reaction is performed preferably at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, in each case per reactor.

In one embodiment, the reaction can be performed in the liquid phase in the presence of a gas phase and, if appropriate, of a solid suspended phase. The hydrogen cyanide and 1,3-butadiene starting materials may in each case be metered in liquid or gaseous form.

In a further embodiment, the reaction can be performed in liquid phase, in which case the pressure in the reactor is such that all feedstocks, such as 1,3-butadiene, hydrogen cyanide and the at least one catalyst, are metered in liquid form, and are present in liquid phase in the reaction mixture. A solid suspended phase may be present in the reaction mixture, which may also be metered in together with the at least one catalyst, for example consisting of degradation products of the catalyst system, comprising, inter alia, nickel(II) compounds.

In process step (a), a stream 1 which comprises 3-pentenenitrile, 2-methyl-3-butenenitrile, the at least one catalyst, stabilizer and unconverted 1,3-butadiene, 1- and 2-butenes, and residues of unconverted hydrogen cyanide is obtained. This stream 1 preferably has the following composition: from 1 to 80% by weight, more preferably from 5 to 50% by weight, of the at least one catalyst, from 0.1 to 50% by weight, more preferably from 1 to 25% by weight, of 1,3-butadiene, from 1 to 80% by weight, more preferably from 10 to 50% by weight, of pentenenitriles, comprising trans-3-pentenenitrile, 2-methyl-3-butenenitrile and further pentenenitrile isomers, and from 0.1 ppm by weight to 10% by weight, more preferably from 1 ppm by weight to 1% by weight, of hydrogen cyanide, based in each case on the total mass of stream 1.

The stream 1 which comprises 3-pentenenitrile, 2-methyl-3-butenenitrile, the at least one catalyst, stabilizer and unconverted 1,3-butadiene, 1- and 2-butenes is subsequently transferred in process step (b) into a distillation apparatus K1. In this distillation apparatus, stream 1 is distilled to obtain a stream 2 rich in 1,3-butadiene and 1- and 2-butenes as the top product, a stream 3 low in 1,3-butadiene as the bottom product, which comprises 3-pentenenitrile, the at least one catalyst, stabilizer and 2-methyl-3-butenenitrile.

Process step (b) of the process according to the invention can be performed in any suitable apparatus known to those skilled in the art. Suitable apparatus for the distillation is the apparatus as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns with structured packing, columns with random packing, or single-stage evaporators such as falling-film evaporators, thin-film evaporators, flash evaporators, multiphase helical tube evaporators, natural circulation evaporators or forced circulation flash evaporators. The distillation can be performed in a plurality of, such as two or three, apparatuses, preferably in a single apparatus.

In a preferred embodiment of the process according to the invention, column internals with structured packing are present in the distillation apparatus, which preferably generate between 2 and 60, more preferably between 3 and 40, in particular between 4 and 20, theoretical plates.

In a particularly preferred embodiment of the process according to the invention, the at least one evaporator stage belonging to the distillation apparatus of process step (b) is designed such that the material to be evaporated suffers a minimum level of thermal damage, as is achieved, for example, by falling-film evaporators, multiphase helical tube evaporators, thin-film evaporators or short-path evaporators by short contact times of the material on the evaporator surface and minimum temperatures of the evaporator surfaces.

In a preferred embodiment of the process according to the invention, the distillation apparatus of process step (b) is operated with a divided column bottom, in which case a circulation stream, which is generally many times larger in relation to stream 3, is conducted from a first column bottom of the distillation column in question to the evaporator, but the liquid effluent stream from the evaporator is not returned directly into the first column bottom, but rather collected in a second column bottom which is separate from the first column bottom, stream 3 is obtained from the second column bottom and the remaining excess from the evaporator circulation stream is allowed to overflow into the first column bottom, and a mixture which is depleted in low boilers compared to the evaporator circulation stream drawn off from the first column bottom is obtained from the second column bottom as stream 3. The evaporator used is preferably a falling-film evaporator.

In a further preferred embodiment of the process according to the invention, the distillation is performed at mean residence times of the liquid phase in the bottom region of the one or more distillation apparatuses in process step (b) of together less than 10 hours, more preferably less than 5 hours, in particular less than 1 hour.

In a further preferred embodiment of the process according to the invention, the condensation at the top of the distillation apparatus is performed in such a way that a substream from the top effluent is flushed back into the condenser.

In a further preferred embodiment of the process according to the invention, the distillation can be performed with a direct condenser, so that the condensation is performed in a column section which is preferably equipped with a structured column packing, a collecting cup below this packing, a liquid draw from the collecting cup, a pumped circulation system with pump and heat exchanger connected to the liquid draw, and at least one device for introducing the liquid pumped in circulation to the packing above the collecting cup.

The distillation apparatus K1 used in process step (b) comprises a distillation column with stripping section, the distillation column having preferably from 2 to 60, more preferably from 3 to 40, in particular from 4 to 20, theoretical plates.

In order to achieve a maximum process yield based on 1,3-butadiene in spite of the only partial reaction in step (a), it is preferred that the 1,3-butadiene-rich stream 2 is recycled into process step (a). However, this recycling is not effected directly into the reactor R. Moreover, not the entire stream 2 is recycled into process step (a).

In process step (d), stream 2 is first condensed in a condenser W1, preferably together with stream 4a from step d). From the condenser, a liquid stream 9 is discharged, which comprises quite predominantly 1,3-butadiene and is conducted partly as reflux to the column K1 (stream 9b), partly in reactor R1 (stream 9a).

1- and 1-butenes accumulate in the circulation of the 1,3-butadiene of the process according to the invention according to how good the efficiency of the recycling is. The more completely 1,3-butadiene is recycled, the sooner the accumulations become noticeable.

Stream 2 is preferably obtained in such a way that it comprises less than 50% by weight, more preferably less than 25% by weight, in particular less than 15% by weight, and preferably more than 1% by weight, more preferably more than 2.5% by weight, in particular more than 5% by weight, of trans-2-butene, cis-2-butene and 1-butene in total. The remainder is essentially 1,3-butadiene.

One means of limiting the accumulation of the butene isomers to the desired value is to discharge a gaseous substream as stream 13 from the condenser W1. This may be associated with losses of 1,3-butadiene, since, on the one hand, the cis-2-butene content in the circulation stream 2 must not rise too high, but, on the other hand, this discharge inevitably always discharges 1,3-butadiene. Stream 13 is preferably withdrawn in gaseous form.

According to the invention, a further means of removing butene isomers from the butadiene circulation is to operate the distillation apparatus K1 in such a way that, below the feed of stream 1, there are active separating stages which permit enrichment of cis-2-butene relative to 1,3-butadiene in stream 3. Instead of a discharge from stream 2, a discharge is then effected in process step (d) in the form of the stream 4b which, as described above in a preferred embodiment, is obtained from stream 3 (FIG. 1).

The discharges are preferably effected in gaseous form.

The absolute pressure in process step (b) is preferably from 0.001 to 100 bar, more preferably from 0.01 to 10 bar, in particular from 0.5 to 5 bar. The distillation is performed in such a way that the temperature in the bottom of the distillation apparatus is preferably from 30 to 140° C., more preferably from 50 to 130° C., in particular from 60 to 120° C. The distillation is performed in such a way that the condensation temperature at the top of the distillation apparatus is preferably from −50 to 140° C., more preferably from −15 to 60° C., in particular from 5 to 45° C. In a particularly preferred embodiment of the process according to the invention, the aforementioned temperature ranges are maintained both at the top and in the bottom of the distillation apparatus.

The reflux ratio at the top of the distillation apparatus is preferably adjusted such that stream 2 comprises from 1 to 1000 ppm, more preferably from 5 to 500 ppm, in particular from 10 to 200 ppm, of 2-methyl-3-butenenitrile.

In process step (b), a 1,3-butadiene-rich stream 2 is obtained as the top product and a stream 3 low in 1,3-butadiene as the bottom product. The designation of the streams as 1,3-butadiene-rich and low-1,3-butadiene is based on the content of 1,3-butadiene in the stream 1 used in process step (b).

In a preferred embodiment of the process according to the invention, the 1,3-butadiene-rich stream 2 comprises a total of from 50 to 100% by weight, more preferably from 80 to 100% by weight, in particular from 85 to 99% by weight, of 1,3-butadiene and butene isomers, and a total of from 0 to 50% by weight, more preferably from 0 to 20% by weight, in particular from 10 ppm by weight to 1% by weight, of pentenenitrile isomers, of which essentially 2-methyl-3-butenenitrile and trans-3-pentenenitrile are present in stream 2.

In a preferred embodiment of the process according to the invention, the low-1,3-butadiene stream 3 comprises a total of from 0 to 50% by weight, more preferably from 1 to 30% by weight, in particular from 2 to 20% by weight, of 1,3-butadiene and butene isomers, and from 1 ppm by weight to 10% by weight, more preferably from 10 ppm by weight to 5% by weight, in particular from 100 ppm by weight to 2% by weight, of stabilizer, based on the total mass of stream 3. In a particularly preferred embodiment of the process according to the invention, the aforementioned specifications for 1,3-butadiene are attained both in stream 2 and in stream 3.

The low-1,3-butadiene stream 3 which stems from process step (b) and comprises 3-pentenenitrile, the at least one catalyst and at least one stabilizer and 2-methyl-3-butenenitrile is subsequently transferred into a distillation apparatus K2 in process step (c). In this distillation apparatus, stream 3 is distilled to obtain a stream 4 as the top product which comprises 1,3-butadiene, a stream 5 at a side draw of the column, which comprises 3-pentenenitrile and 2-methyl-3-butenenitrile, and a stream 6 as the bottom product, which comprises the at least one catalyst and at least one stabilizer.

Process step (c) of the process according to the invention can be performed in any suitable apparatus known to those skilled in the art. Suitable apparatus for this distillation is the apparatus as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns with structured packing, columns with random packing, or single-stage evaporators such as falling-film evaporators, thin-film evaporators, flash evaporators, multiphase helical tube evaporators, natural circulation evaporators or forced circulation flash evaporators. The distillation can be performed in a plurality of, such as two or three, apparatuses, preferably in one apparatus.

In a particularly preferred embodiment, the distillation apparatus selected in process step (c) is at least one distillation column which comprises a stripping section, more preferably only one distillation column which has only one stripping section.

The distillation apparatus is preferably equipped with a structured packing which generates from 2 to 50, more preferably from 3 to 40, in particular from 4 to 30, theoretical plates.

In a particularly preferred embodiment of the process according to the invention, the at least one evaporator stage belonging to the distillation apparatus of process step (c) is designed such that the material to be evaporated suffers a minimum level of thermal damage, as is achieved, for example, by falling-film evaporators, multiphase helical tube evaporators, thin-film evaporators or short-path evaporators by short contact times of the material on the evaporator surface and minimum temperatures of the evaporator surfaces.

In a further preferred embodiment of the process according to the invention, the distillation is performed at mean residence times of the liquid phase in the bottom region of the distillation apparatuses in process step (c) of together less than 10 hours, more preferably less than 5 hours, in particular less than 1 hour.

In a particularly preferred embodiment of the process according to the invention, the distillation is performed at mean residence times of the liquid phase in the bottom region of the distillation apparatuses in process steps (b) and (c) of together less than 10 hours, more preferably less than 5 hours, in particular less than 1 hour.

The absolute pressure in process step (c) is preferably from 0.001 to 10 bar, more preferably from 0.010 to 1 bar, in particular from 0.020 to 0.5 bar. The distillation is performed in such a way that the temperature in the bottom of the distillation apparatus is preferably from 30 to 140° C., more preferably from 40 to 130° C., in particular from 50 to 120° C. The distillation is performed in such a way that the condensation temperature at the top of the distillation apparatus is preferably from −20 to 140° C., more preferably from −10 to 80° C., in particular from −5 to 60° C. In a particularly preferred embodiment of the process according to the invention, the aforementioned temperature ranges are maintained both at the top and in the bottom of the distillation apparatus.

In the distillation of process step (c), a stream 4 is obtained as the top product. This stream 4 comprises preferably a total of from 50 to 100% by weight, more preferably from 80 to 100% by weight, in particular from 90 to 99.9% by weight, of 1,3-butadiene and butene isomers, and a total of from 0 to 50% by weight, more preferably from 0 to 20% by weight, in particular from 10 ppm by weight to 10% by weight, of pentenenitrile isomers, of which essentially 2-methyl-3-butenenitrile and trans-3-pentenenitrile are present in stream 4.

The content of trans-2-butene, cis-2-butene and 1-butene in total in stream 4 or 4a is preferably more than 2% by weight, more preferably more than 10% by weight, in particular more than 15% by weight, and preferably less than 80% by weight, more preferably less than 70% by weight.

Stream 4, which is obtained in the distillation apparatus K2 in process step (c), is preferably drawn off in vaporous form and compressed with a compression apparatus V1 and with pressure elevation. This affords a compressed stream 4.

From stream 4, a substream 4b which consists of 1- and 2-butenes as well as 1,3-butadiene is discharged in liquid or gaseous form.

The compressed main stream 4a, which still comprises 1,3-butadiene, is condensed in the condenser W1.

The bottom product obtained in process step (c) is a stream 6 which comprises the at least one catalyst, the at least one stabilizer, and also 3-pentenenitriles and 2-methyl-3-butenenitrile. The proportion of pentenenitrile isomers in stream 6 is a total of preferably from 0.1 to 80% by weight, more preferably from 5 to 50% by weight, in particular from 10 to 40% by weight, based in each case on stream 6.

In addition, it is particularly preferred that stream 6 is recycled at least partly into process step (a) of the hydrocyanation (stream 6*b*). It is possible that the recycled catalyst is subjected partly to a regeneration, for example as described in German patent application DE 10 35 10 02 with the title "Einsatz von azeotrop-getrocknetem Nickel(II)-halogenid" [Use of azeotropically dried nickel(II) halide] to BASF Aktiengesellschaft.

In a preferred embodiment of the process according to the invention, the content of 2-methyl-3-butenenitrile in this recycled stream 6 is less than 10% by weight, more preferably less than 5% by weight, in particular less than 1% by weight. This is achieved by providing sufficient distillative separating stages between the draw point for stream 5 and the draw point for stream 6.

In a preferred embodiment, the thermal stress of the catalyst can be kept low by virtue of the bottom temperature not exceeding 140° C., which can be ensured by suitable pressure conditions.

In addition, it is also possible to use stream 6 from process step (c) completely or partly as a catalyst stream for other hydrocyanations, for example for the hydrocyanation of 3-pentenenitrile. Even when catalyst stream 6 is used for the hydrocyanation of 3-pentenenitrile, it is preferred that the content of 2-methyl-3-butenenitrile in this catalyst stream 6 is minimized and does not exceed the aforementioned values.

In a further preferred embodiment, a fresh catalyst stream is conducted into the distillation apparatus of process step (c) in order to be able to control the pentenenitrile content of the overall catalyst stream to process step (a) within the above-specified limits.

In a further preferred embodiment of the process according to the invention, the amount of catalyst discharge and hence the necessary supplementary amount of fresh catalyst is such that the content of methylglutaronitrile in the catalyst circulation does not rise above 50% by weight, more preferably not above 20% by weight, in particular not above 10% by weight, based in each case on the catalyst circulation stream, in order to have the catalyst stream discharged in each case present in a regeneration with a minimum level of inhibiting effects of methylglutaronitrile for the uptake of nickel(0).

In a further preferred embodiment of the process according to the invention, the amount of catalyst discharge and hence the necessary supplementary amount of fresh catalyst is such that the content of nickel(0) complexes in the catalyst circulation does not fall below 0.05% by weight, more preferably not below 0.1% by weight, in particular not below 0.2% by weight, based in each case on the catalyst circulation and in each case calculated as metallic nickel(0), in order to ensure the activity of the hydrocyanation catalyst in spite of losses of nickel(0) complexes during the reaction in step (a) or during the distillation processes in step (b) and (c), in particular during the reaction in step (a).

In a further preferred embodiment of the process according to the invention, it is possible to transfer stream 1, which is obtained in process step (a), directly into process step (c) with exclusion of process step (b).

Figure 2:
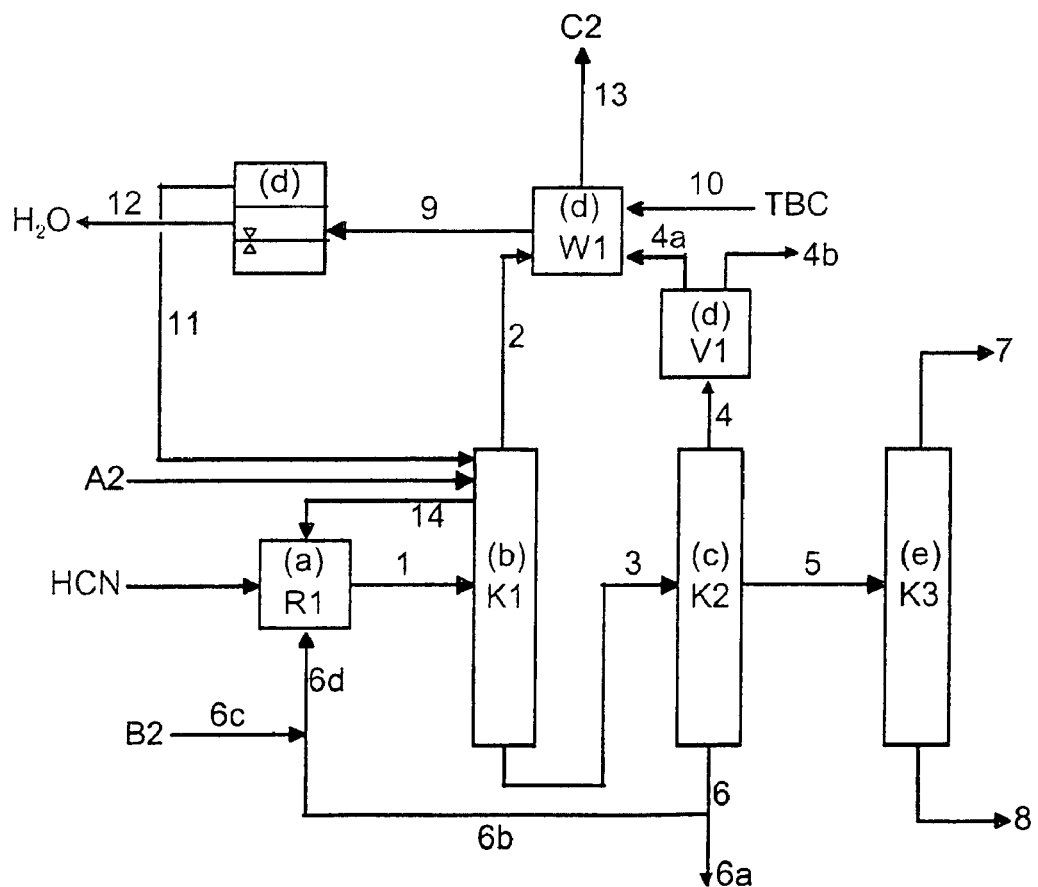
FIG. 2 is a schematic diagram depicting another embodiment of a process for preparing 3-pentenenitrile by hydrocyanating 1,3-butadiene in which the drying of 1,3-butadiene is shifted into process step (b).

In a particularly preferred process variant, the column K4 used in process step (b') (FIG. 1) is omitted. FIG. 2 demonstrates that, instead of this, the drying of the 1,3-butadiene is shifted into process step (b) (top of column K1).

This process comprises the following process steps (FIG. 2):

(a) reaction of dried 1,3-butadiene, which is passed as stream 14 from a side draw of column K1 into reactor R1, with hydrogen cyanide over at least one catalyst to obtain a stream 1 which comprises 3-pentenenitrile, 2-methyl-3-butenenitrile, the at least one catalyst, 1,3-butadiene, and 1- and 2-butenes, with or without residues of unconverted hydrogen cyanide, (b) distillation of stream 1 in a distillation apparatus K1 by feeding 1,3-butadiene comprising water, 1- and 2-butenes and a stabilizer in the region between top and side draw of the column to obtain a stream 2 as the top product, stream 14 as the side draw and a stream 3 as the bottom product which comprises 3-pentenenitrile, the at least one catalyst, 2-methyl-3-butenenitrile and the remaining portion of the 1,3-butadiene from stream 1 which has not been removed in stream 2, (c) distillation of stream 3 in a distillation apparatus K2 to obtain a stream 4 as the top product, which 1,3-butadiene and 1- and 2-butenes, a stream 5 at a side draw of the column, which 3-pentenenitrile and 2-methyl-3-butenenitrile, and a stream 6 as the bottom product, which comprises the at least one catalyst, (d) condensation of stream 2 from distillation apparatus K1 and the stream 4*a* which has been compressed in one compressor V1 or a plurality of compressors from distillation apparatus K2 into a condenser W1 or a plurality of condensers, transfer of the resulting condensate as stream 9 into a phase separation apparatus, transfer of the upper liquid phase consisting of 1,3-butadiene as stream 11 to the top of the distillation apparatus K1, and discharge of the lower liquid aqueous phase as stream 12, (e) distillative separation of stream 5 to obtain 3-pentenenitrile and 2-methyl-3-butenenitrile.

In process step (e), stream 5 is transferred into a further distillation apparatus K3. In this distillation apparatus, stream 5 is distilled to obtain a stream 7 which comprises 2-methyl-3-butenenitrile, and a stream 8 which comprises 3-pentenenitrile. Stream 7 is obtained at the top of the distillation apparatus, while stream 8 is obtained in the bottom of the distillation apparatus. The process can be performed, for example, in a manner known per se according to DE 10 2004 04724.

In a particularly preferred embodiment of the process according to the invention, the stream 5 which may be obtained as a gaseous side draw is transferred in gaseous form into the distillation apparatus K3 of process step (e), the pressure at the position of the feedpoint for stream 5 in the distillation apparatus of process step (e) being less than or equal to the pressure at the position of the side draw for stream 5 in the distillation apparatus of process step (c).

The scope of this description does not exclude process variants in which the pressure of stage (e) is selected freely and gas stream 5, if appropriate, is compressed to a higher pressure than at the withdrawal point in (c), or is liquefied by condensation and, if appropriate, conveyed with a pump in order to be fed to stage (e).

Process step (e) of the process according to the invention can be performed in any suitable apparatus known to those skilled in the art. Suitable apparatus for this distillation is the apparatus as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns with structured packing, columns with random packing, or single-stage evaporators such as falling-film evaporators, thin-film evaporators, flash evaporators, multiphase helical tube evaporators, natural circulation evaporators or forced circulation flash evaporators. The distillation can be performed in a plurality of, such as two or three, apparatuses, preferably in a single apparatus.

The columns preferably comprise structured packings. The structured packings generate preferably from 5 to 100, more preferably from 10 to 80, in particular from 15 to 50, theoretical plates.

The pressure in process step (e) is preferably from 0.001 to 100 bar, more preferably from 0.01 to 20 bar, in particular from 0.05 to 2 bar. The distillation is performed in such a way that the temperature in the bottom of the distillation apparatus is preferably from 30 to 250° C., more preferably from 50 to 200° C., in particular from 60 to 180° C. The distillation is performed such that the condensation temperature at the top of the distillation apparatus is preferably from −50 to 250° C., more preferably from 0 to 180° C., in particular from 15 to 160° C. In a particularly preferred embodiment of the process according to the invention, the aforementioned temperature ranges are maintained both at the top and in the bottom of the distillation apparatus. In one embodiment of the process according to the invention, stream 7, which is obtained in process step (e), is fed to an isomerization according to DE-A-102 004 004 671.

In one embodiment of the process according to the invention, stream 7, which is obtained in process step (e), can be recycled into process step (a) and/or into process step (b), in which case the reaction conditions in process step (a) or the residence time of the liquid phase in the bottom of process step (b) are selected such that 2-methyl-3-butenenitrile is isomerized at least partly to trans-3-pentenenitrile.

In a further embodiment of the process according to the invention, stream 7 is obtained as a side draw stream in the distillation apparatus of process step (e), the top product obtained from this distillation column being a stream which, as well as 2-methyl-3-butenenitrile, comprises essentially also (Z)-2-methyl-2-butenenitrile, with or without 1,3-butadiene and butene isomers, and also vinylcyclohexene and ethylidenecyclo-hexene. This embodiment is advantageous, since stream 7 is then richer in 2-methyl-3-butenenitrile than the top stream.

The content of trans-3-pentenenitrile in stream 7 is preferably from 0 to 50% by weight, more preferably from 100 ppm by weight to 20% by weight, in particular from 1 to 15% by weight. The content of 2-methyl-3-butenenitrile in stream 8 is preferably from 0 to 10% by weight.

The process according to the invention enables the preparation of 3-pentenenitrile and 2-methyl-3-butenenitrile in an integrated process which, owing to the recycling, which is possible to a virtually complete degree, of the 1,3-butadiene streams and of the catalyst stream, has a high process yield for the feedstocks. The temperatures and pressure conditions needed for the distillative removal of 1,3-butadiene and pentenenitrile isomers from the catalyst-containing streams can be selected such that, firstly, the bottom evaporator temperatures when the process is practiced on the production scale with technically achievable residence times are so low that they preferably do not lead to catalyst damage, and that, on the other hand, the condensation of the top products of the particular distillation steps takes place preferably at temperatures at which heat removal on the production scale is possible with economically acceptable cost and inconvenience.

It is also novel and inventive that stabilizer-containing butadiene which is dried by azeotropic distillation can be used. When an aqueous stabilizer solution (stream 10) is additionally introduced into the compressor(s) and/or condenser(s) in stage (d), the risk of butadiene polymerization does not occur at any point in the process.

Accumulation of stabilizer does not occur, since, as described in U.S. Pat. No. 3,773,809, it is conducted via a purge stream to the catalyst extraction and is discharged there with the lower phase (ADN phase) in the phase separation.

If hydrogen cyanide conducted into the reactor R1 is not converted completely, there is no risk that it gets into the workup stages and causes solid deposits comprising $Ni(CN)_2$ there. Instead, a butadiene/hydrocyanic acid low boiler azeotrope forms. The hydrocyanic acid gets into the top draw of column K1 and is conducted via the condenser W1 into the apparatus for phase separation. It is discharged from the process together with the liquid aqueous phase.

Explanation of symbols in FIG. 1 and FIG. 2

FIG. 1:
A 1=aqueous fresh butadiene+TBC
B 1=dried butadiene+TBC
C 1=fresh catalyst supplementation
D 1=offgas comprising a low level of butadiene FIG. 2:
A 2=aqueous fresh butadiene+TBC
B 2=fresh catalyst supplementation
C 2=offgas comprising a low level of butadiene

The invention claimed is:

1. A process for preparing 3-pentenenitrile by hydrocyanating 1,3-butadiene, which comprises the following process steps:

(b') distillation of 1,3-butadiene comprising water, 1- and 2-butenes and a stabilizer in a distillation apparatus K4 to obtain a stream 15 as the bottom product, which comprises dried 1,3-butadiene, 1- and 2-butenes and the stabilizer, and a stream 16 as the top product, which comprises an azeotropic 1,3-butadiene/water mixture, condensation of the stream 16 in a condenser W, transfer of the resulting condensate (stream 17) into a phase separation apparatus, recycling of the upper liquid phase (stream 18) consisting of 1,3-butadiene as reflux to the column K4, and discharge of the lower liquid aqueous phase (stream 19), (a) reaction of stream 15 in a reactor R1 with hydrogen cyanide over at least one catalyst (stream 6d) to obtain a stream I which comprises 3-pentenenitrile, 2-methyl-3-butenenitrile, the at least one catalyst in the form of homogeneously dissolved nickel complexes or nickel(0) complexes and phosphorus ligands, unconverted 1,3-butadiene, and 1- and 2-butenes, with or without residues of unconverted hydrogen cyanide, (b) distillation of stream 1 in a distillation apparatus K1 to obtain a stream 2 as the top product, which comprises the predominant portion of the 1,3-butadiene from stream 1, and to obtain a stream 3 as the bottom product, which comprises 3-pentenenitrile, the at least one catalyst, 2-methyl-3-butenenitrile, 1- and 2-butenes and the remaining proportion of the 1,3-butadiene from stream 1 which has not been removed in stream 2, (c) distillation of stream 3 in a distillation apparatus K2 to obtain a stream 5 at a side draw of the column, which 3-pentenenitrile and 2-methyl-3-butenertitrile, a stream 6 as the bottom product, which comprises the at least one catalyst, and a stream 4 as the top product, (d) compression of stream 4 in the compressor VI, discharge of a gaseous substream 4b which comprises 1- and 2-butenes, transfer of the compressed stream 4a into the condenser W1, combined cond. With stream 2 from b) in combined condensation of this stream 2 from b) and transfer of the condensate as stream 9, partly as reflux to the column K1 (stream 9b), partly as return stream into the reactor R1 (stream 9a), and (e) distillative separation of stream S to obtain 3-pentenenitrile and 2-methyl-3-butenenitrile.

2. A process for preparing 3-pentenenitrile by hydrocyanating 1,3-butadiene, which comprises the following process steps:
   (a) reaction of dried 1,3-butadiene, which is passed as stream 14 from a side draw of column K1 into reactor R1, with hydrogen cyanide over at least one catalyst to obtain a stream 1 which comprises 3-pentenenitrile; 2-methyl-3-butenenitrile, the at least one catalyst in the form of homogeneously dissolved nickel complexes or nickel(0) complexes and phosphorus ligands, 1,3-butadiene, and 1- and 2-butenes, with or without residues of unconverted hydrogen cyanide,
   (b) distillation of stream 1 in a distillation apparatus K1 by feeding 1,3-butadiene comprising water, 1- and 2-butenes and a stabilizer in the region between top and side draw of the column to obtain a stream 2 as the top product, stream 14 as the side draw and a stream 3 as the bottom product which comprises 3-pentenenitrile, the at least one catalyst, 2-methyl-3-butenenitrile and the remaining portion of the 1,3-butadiene from stream 1 which has not been removed in stream,
   (c) distillation of stream 3 in a distillation apparatus K2 to obtain a stream 4 as the top product, which 1,3-butadiene and 1- and 2-butenes, a stream 6 at a side draw of the column, which 3-pentenenitrile and 2-methyl-3-butenenitrile, and a stream 6 as the bottom product, which comprises the at least one catalyst,
   (d) condensation of stream 2 from distillation apparatus K1 and the stream 4a which has been compressed in one compressor V1 or a plurality of compressors from distillation apparatus K2 into a condenser W1 or a plurality of condensers, transfer of the resulting condensate as stream 9 into a phase separation apparatus, transfer of the upper liquid phase consisting of 1,3-butadiene as stream 11 to the top of the distillation apparatus K1, and discharge of the lower liquid aqueous phase as stream 12, and
   (e) distillative separation of stream 5 to obtain 3-pentenenitrile and 2-methyl-3-butenenitrile.

3. The process according to claim 1, wherein, in process step (d), an aqueous solution of at least one butadiene stabilizer is introduced into the compressor(s) and/or condenser(s).

4. The process according to claim 2, wherein, in process step (d), an aqueous solution of at least one butadiene stabilizer is introduced into the compressor(s) and/or condenser(s).

5. The process according to claim 1, wherein a substream 6a which comprises the at least one catalyst and at least one butadiene stabilizer is discharged from stream 6.

6. The process according to claim 2, wherein a substream 6a which comprises the at least one catalyst and at least one butadiene stabilizer is discharged from stream 6.

7. The process according to claim 3, wherein a substream 6a which comprises the at least one catalyst and at least one butadiene stabilizer is discharged from stream 6.

8. The process according to claim 1, wherein unconverted hydrogen cyanide is discharged from the phase separation apparatus with stream 19.

9. The process according to claim 2, wherein unconverted hydrogen cyanide is discharged from the phase separation apparatus with stream 12.

* * * * *

UNITED STATES PATENT AND TRADEMARK OFFICE
CERTIFICATE OF CORRECTION

PATENT NO. : 8,058,466 B2
APPLICATION NO. : 12/376731
DATED : November 15, 2011
INVENTOR(S) : Haderlein et al.

It is certified that error appears in the above-identified patent and that said Letters Patent is hereby corrected as shown below:

In claim 2, at column 19, line 21, "stream," should be replaced with --stream 2,--

Signed and Sealed this
Fifteenth Day of May, 2012

David J. Kappos
*Director of the United States Patent and Trademark Office*